United States Patent
Ray et al.

(10) Patent No.: US 6,203,296 B1
(45) Date of Patent: Mar. 20, 2001

(54) MINIATURE PERISTALTIC PUMP

(75) Inventors: Claude Ray, Montezillon (CH); Christian Taillard, Les Fins (FR)

(73) Assignee: Counseil-Ray S.A. (CH)

( * ) Notice: Subject to any disclaimer, the term of this patent is extended or adjusted under 35 U.S.C. 154(b) by 0 days.

(21) Appl. No.: 09/254,580

(22) PCT Filed: Sep. 8, 1997

(86) PCT No.: PCT/CH97/00329

§ 371 Date: Mar. 8, 1999

§ 102(e) Date: Mar. 8, 1999

(87) PCT Pub. No.: WO98/11350

PCT Pub. Date: Mar. 19, 1998

(30) Foreign Application Priority Data

Sep. 10, 1996 (FR) .................................................. 96 11171

(51) Int. Cl.[7] .................................................. F04B 43/12
(52) U.S. Cl. .................................... 417/477.7; 417/477.2; 417/477.8; 417/477.9
(58) Field of Search ............................ 417/477.7, 477.8, 417/477.9, 477.2, 477.6

(56) References Cited

U.S. PATENT DOCUMENTS

| | | | |
|---|---|---|---|
| 3,249,059 | * | 5/1966 | Renn .................................. 417/477.6 |
| 5,741,125 | * | 4/1998 | Neftel et al. ....................... 417/477.7 |
| 5,788,671 | * | 8/1998 | Johnson ............................. 604/131 |
| 5,928,196 | * | 7/1999 | Johnson et al. ................... 604/153 |

* cited by examiner

Primary Examiner—Charles G. Freay
Assistant Examiner—Cheryl J. Tyler
(74) Attorney, Agent, or Firm—Baker Botts L.L.P.

(57) ABSTRACT

A miniature peristaltic pump includes a rotor with three turning rollers, a support piece with a rounded portion arranged substantially concentric to the rotor and against which, when operating, the rollers are brought to compress a flexible tubing connected to a reservoir of solution to push it outwards and for automatically compensating positional deviations between the roller and the support piece. Each roller has a substantially cylindrical body and a shaft on which the body is rotatably mounted. The ends of the roller shafts are located in oblong slots radially recessed in the rotor. The compensating device includes two springs arranged at the respective ends of the shafts and have a central port concentric to the rotor and three curved spring arms, one for each roller, with one end connected to the central part and the other end bearing on the corresponding end of a roller shaft to push it outwards and thus enable it to exert a substantially constant force of pressure.

22 Claims, 6 Drawing Sheets

MINIATURE PERISTALTIC PUMP

This invention refers to peristaltic pumps. More specifically, it concerns a miniature peristaltic pump for the injection of drug solutions.

Miniature pumps or micropumps for medical use have been available for several years. Light and of small size, they can be worn discreetly and comfortably by the patient and permit the administration of controlled quantities of drug solutions to said patient, either subcutaneously or intravenously, continuously or according to a specific program, without his having to be confined to bed or hooked up to a cumbersome, costly and noisy machine.

Such pumps are most often of the rotary peristaltic type whose principle consists in having a flexible plastic tubing connected to a reservoir containing the solution and having it pressed locally against a rounded-off support piece by means of pressure rollers mounted on a rotor driven by a motor operating through a gear train. The liquid is thus drawn up from the reservoir and discharged toward the outlet to be injected into the patient.

Patents EP 388 787, EP 447 909, EP 521 184 and WO 94/06491 describe miniature peristaltic pumps of this type.

When designing such pumps, it is particularly important to carefully optimize the coupling between the rollers and the tubing being pressed by the rollers the one after the other against the support piece.

Measurements have shown that the minimum pressure on a roller having a diameter of 5 mm, necessary to make a liquid flow in plastic tubing with an internal diameter of 1.47 mm and an external diameter of 1.96 mm is 95 grams. The corresponding tensile force exerted by the roller is 15 grams. The pressure on the roller may increase up to 150 grams without proportionally increasing the tensile force, which then only increases from 15 to 20 grams. However, beyond that limit, the tensile force increases very rapidly. In fact, it increases to 50 grams for a pressure of 200 grams, after which measurements become impossible.

Such observations are easily explained by the fact that once the flexible tubing has been squeezed until it is completely sealed, any increase in pressure causes deformation of the plastic material and the corresponding tensile force then increases in relation to its elasticity module.

Thus, any variation in the position of the roller in relation to the tubing beyond that which achieves its closure, puts a heavy load on the roller-carrying rotor and its driving motor, which quickly causes jamming and therefore stopping of the pump. The effect is all the more pronounced in the miniature pumps that are obviously equipped with less powerful motors than the nonportable pumps.

Contrary to that, any variation in the position of the roller below the one that enables the complete closure does not permit a sufficient flow of the liquid.

It is thus very important, in order to obtain a reliably functioning pump, that the distance separating the roller from the support piece be perfectly maintained and kept constant in order to avoid jamming or irregular and insufficient output.

Thus, if the support piece and the roller are fixed, extremely strict manufacturing tolerances are necessary and this therefore raises the cost price of the pump quite appreciably.

It is therefore preferable to accept lighter tolerances and to provide a means which automatically adjusts any gap in position between the support piece and the roller.

Patents EP 388 787 and EP 447 909, already referred to, succinctly describe arrangements to resolve this problem.

Patent EP 388 787 shows a support piece which has the shape of a hook articulated at one of its ends by a pin and presses against the tubing by means of a screw-compressed spring. This support piece, being almost always acted upon by two rollers, cannot ensure the correct adjustment of the position gaps for each of the separate rollers.

Patent EP 477 909 shows that the rollers are mounted on their axis with a slight radial play permitting them a certain clearance and that individual leaf springs acting directly on their central part push them towards the outside. Such an arrangement presents the double drawback of complicating the mounting of the rotor and to cause it to slide on the tubing rather than to turn. It is also shown in this document that the springs can be replaced by a unique elastic part, for which no description is supplied, and that they can be definitely omitted because the rollers are then radially displaced by the inherent elasticity of the tubing itself. This shows that the magnitude of the problem has not been fully understood.

Other solutions to compensate the position gaps between the rollers at their support piece have been disclosed in patents U.S. Pat. No. 4,950,136 and CH 562 402. In the described embodiments, each one of the two cylindrical rollers is mounted on a shaft, the ends of which are fitted into oblong openings of the rotor. In the US patent, two semi-circular springs act by their ends upon each end of the shaft to push it toward the outside. In the CH patent, one single semi-circular spring is provided. Such arrangements are however limited to pumps having two rollers.

The so-called cassette pumps are the most common in medical applications. They comprise two parts, on the one hand the actual pump with the motor, the drive electronics, the battery and the pump head formed by the rotor and the pressure rollers and, on the other, the cassette which clips onto the pump and includes the tubing and the support piece. The reservoir is either integrated into the cassette when it is of a small size, or arranged outside when the size is larger.

The pumps in Patents EP 447 909, EP 521 184 and WO 94/06491 are of this variety.

In these three cases, the cassette, which is assembled in a permanent manner, includes the tubing, the support piece and the reservoir. The pumps of the two EP patents are single-use-only because, once connected, the two units cannot be disconnected. At the end of treatment or when the cassette is empty, the entire unit is discarded, including the motor, the pump head, the support piece, the gear train and the circuit which are all still capable of functioning again. As far as the pump in the WO Patent is concerned, its cassette may be discarded at the same time as its reservoir. Thus, in these three pumps, components are being discarded which could still be used as they are because they are not worn out and have never been in contact with the medication injected into the patient.

Documents U.S. Pat. No. 4,817,057 and EP 120 284, moreover, describe peristaltic pumps with large size cassettes, i.e. non-portable ones. Even though the tubing can easily be inserted into, or removed from the cassette, it is fitted with a connecting nozzle to the tubing coming from the reservoir and its part that is subjected to the peristaltic action is specially designed to withstand the prolonged exposure to the compression effect of the rollers. Such a design has drawbacks because, not only does it not permit the re-use of the tubing to administer different drug solutions to different patients, but furthermore, the interconnecting operations of the two tubings increase the risk of bacterial contamination of the circuit.

Another major problem occurs during the design of such pumps. The problem is the discharging of the tubings, i.e.

the discharge of the air still contained in the tubings, before inserting the needle into the patient. The rotor's rotation speed being very slow, generally less than 1 rpm, this operation must, in order not to take too much time, be done by making the rotor turn rapidly by external means. Patent EP 388 787 discloses a wheel which is part of the rotor and includes a series of holes into which one can put, for example, the point of a ballpoint pen to turn the wheel rapidly. That solution is certainly an interesting one, but no arrangement has been provided to keep this operation from damaging the gear train.

The object of the invention is to provide an improved miniature peristaltic pump that is free of the drawbacks of pumps known in the prior art.

The miniature peristaltic pump according to the invention includes:

a rotor equipped with three rotating rollers comprising a substantially cylindrical body and a shaft on which said body is rotatably mounted, the ends of the shafts of the rollers being fitted into oblong openings arranged radially in the rotor, a means for driving said rotor, a means for controlling said driving means, a support piece equipped with a rounded-off portion arranged in a substantially concentric manner to the rotor and against which, during operation, said rollers compress a flexible tubing connected to a solution reservoir to push the solution towards the outside and a means for automatically compensating, by means of springs, the gaps in position between the rollers and said support piece.

This pump is characterized in that said means for automatically compensating includes two springs arranged at the level of the respective ends of said shafts and comprise a central part concentric to the rotor and three curved spring arms, one for each roller, of which one end is connected to said central part and the other end is supported on the corresponding end of a roller shaft to push it towards the outside, thus permitting it to exert a substantially constant compression force on the tubing.

Other characteristics of this invention are described in the specification to follow, which is based on the attached drawings and show, for explanatory but not restrictive purposes, a preferred design form of this pump. On these drawings.

Figure 12:
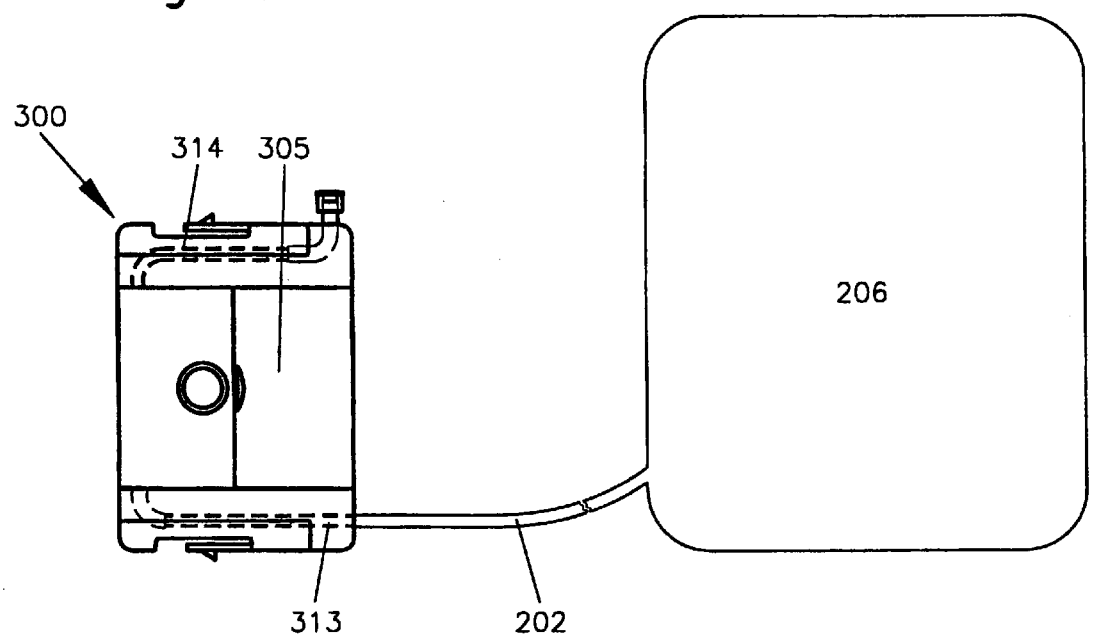

Finally, FIG. 12 illustrates an other embodiment of the reservoir unit.

As shown by FIGS. 1 through 5, the miniature pump according to the invention is composed of three units, a pump unit 100, a reservoir unit 200, and a cassette unite 300, which will also be called pump, reservoir and cassette respectively. Reservoir 200 fits in a manner that permits removal into cassette 300 which, in turn, connects in the same manner to pump 100.

To get an idea and simply as an example, the assembled pump is 110 mm long, 55 mm wide and 13 mm thick for a reservoir capacity of 10 ml.

Figure 1:
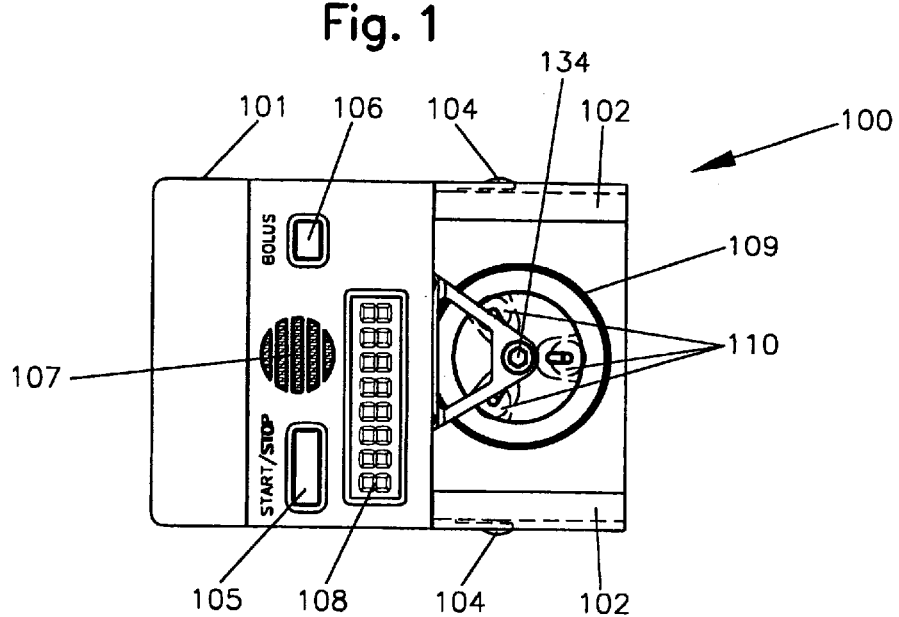
FIG. 1 is a general external view of the pump unit.

The pump unit 100, shown in FIG. 1, includes a rigid plastic case 101, the bottom of which extends on one side to form the base for two parallel sliders 102 that hold the cassette unit 300 like a drawer. As clearly shown in FIG. 5, each slider 102 is pierced by an opening 103 into which is fitted a first flexible tongue 104 which forms a push button intended to release the cassette when it needs to be disconnected from the pump.

On its top surface, the case 101 has a 'START/STOP' button 105 which controls the starting and stopping of the pump, a 'BOLUS' button 106 which activates the administration of additional doses of solution, a sound alarm 107 and an LCD (liquid crystal display) 108. Between its two sliders 102, case 101 shows a rotor 109 having three rollers 110, thus forming the pump head. A more detailed description of it will be given below, along with that of its driving means.

Figure 2:
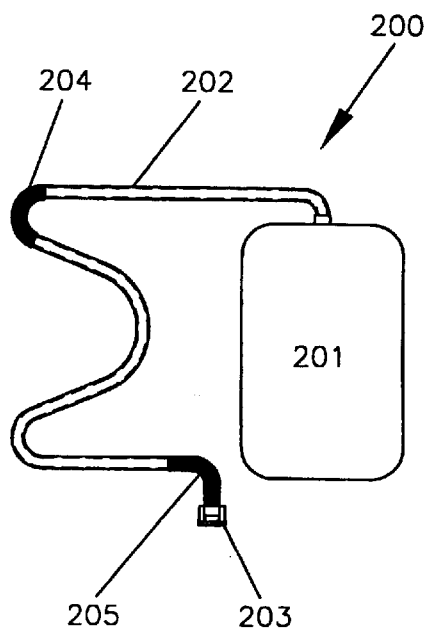
FIG. 2 represents the reservoir unit.

The reservoir unit 200, shown in FIG. 2, is formed by a plastic bag 201 having a volume of 10 ml in the embodiment shown and flexible plastic tubing 202 of which one end is connected to the bag and the other, intended for connection to a subcutaneous or intravenous injection needle, is sealed by a stopper 203. The tubing furthermore includes two rigid reinforced elbow-shaped first and a second connectors 204 and 205 that serve to clip it into the cassette 300, as will be more easily seen later on.

Figure 3:
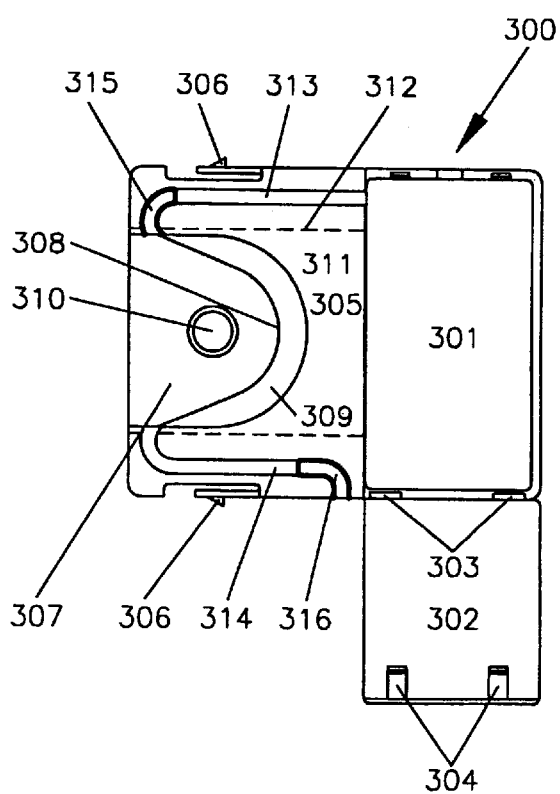
FIG. 3 represents the cassette unit.

The cassette unit 300, as seen from below in FIG. 3, is mad of rigid plastic and includes a first housing 301 intended to accommodate the plastic bag 201. It has more or less the same thickness and the same width as case 101 and has a cover 302 on the bottom, mounted on two hinges 303 and provided, at the other end, with second tongues 304, which assure its closure by clipping. First housing 301 is extended by a plate 305 shaped and sized to fit, like a drawer, between the sliders 102 of the case. Two third and fourth tongues 306, arranged on their sides, permit its clipping-in by the securing of their ends into openings 103, also shown in FIG. 5.

Plate 305 is perforated on the bottom side by a second housing 307, of a general U shape, sized to accommodate the rotor 109 of the pump unit. To this end, it includes a central rounded-off part 308 of approximately 120 degrees, whose radius is slightly greater than that of the ring which covers the outside radius of rollers 110. It is on this rounded-off portion 308 that the three rollers successfully compress the flexible tubing 202 during operation. An additional rounded-off clearance 309 is provided around portion 308 to accommodate the lower part of rotor 109, of a larger diameter than the ring covered by the rollers, as will become apparent later on.

The bottom of the second housing 307 which forms the top surface of the unit is pierced at the center of the rounded-off portion 308 by a circular opening 310 which is the location where the shaft of rotor 109 first in order to permit discharging the pump before use, as will be described later on. This opening can be closed off by a cover 311 sliding in a hollow space 312 of the upper wall of the unit.

Plate 305 also includes two channels 313 and 312, each arranged at the bottom of one of its sides parallel to the bottom. Channel 313 connects the first housing 301 to the front part of the second housing 307. Before it emerges in the second housing 307, it comprises a first elbowed section 315, of a larger diameter, formed and sized in such a way as to fit and maintain the first rigid connector 204 of flexible tubing 202 by clipping. Channel 314 begins at the front part of the second housing 307 at a location oppose from the location where the other channel arrives, and emerges outside after a second elbowed section 316, which is of a larger diameter, as is formed and sized so as to accommodate and maintain the second rigid connector 205 of tubing 202 by clipping.

Figure 5:
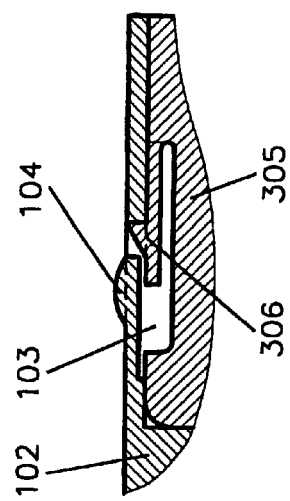
FIG. 5 is a cross-section detail of FIG. 4 after connection has been made.
Figure 4:
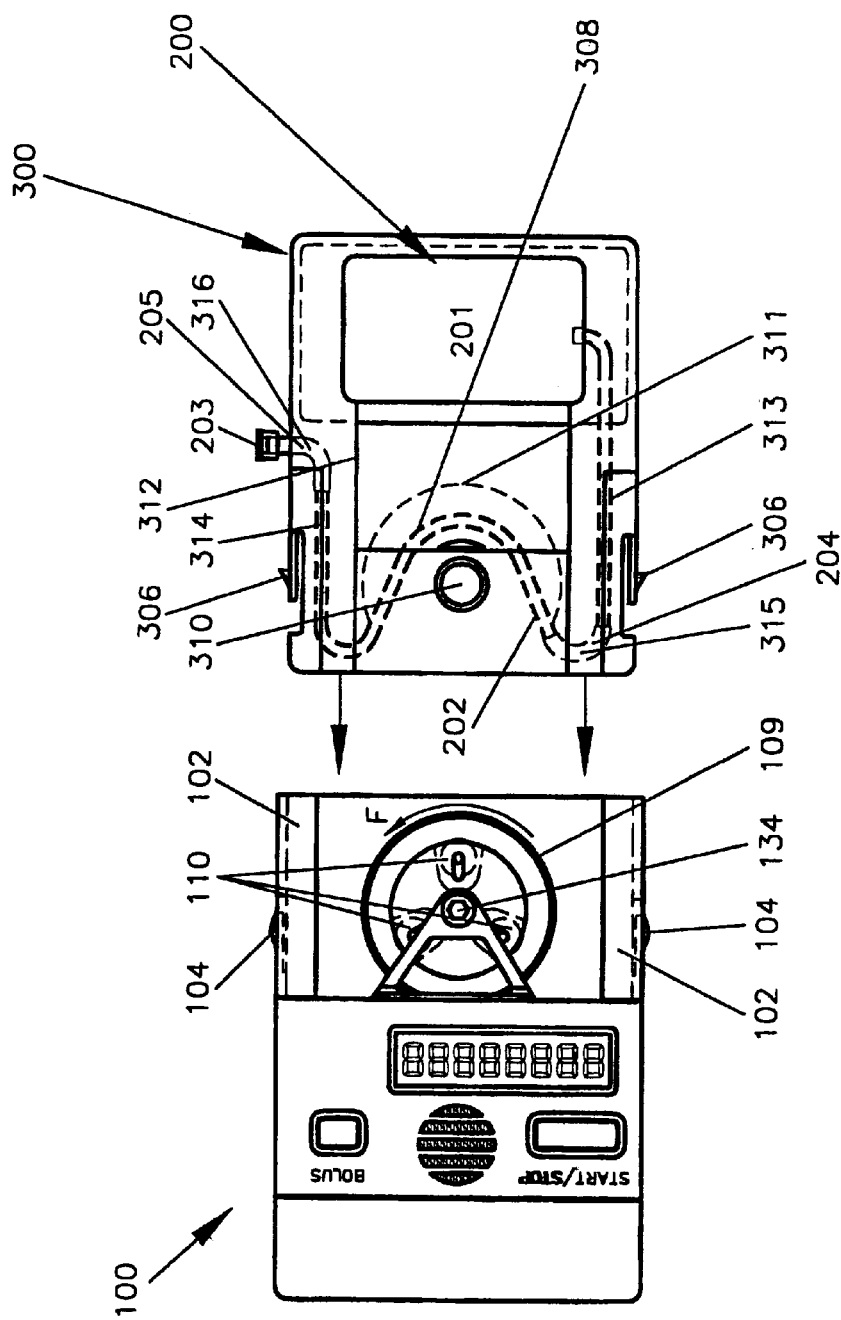
FIG. 4 shows the manner in which the three units are connected.
Figure 6:
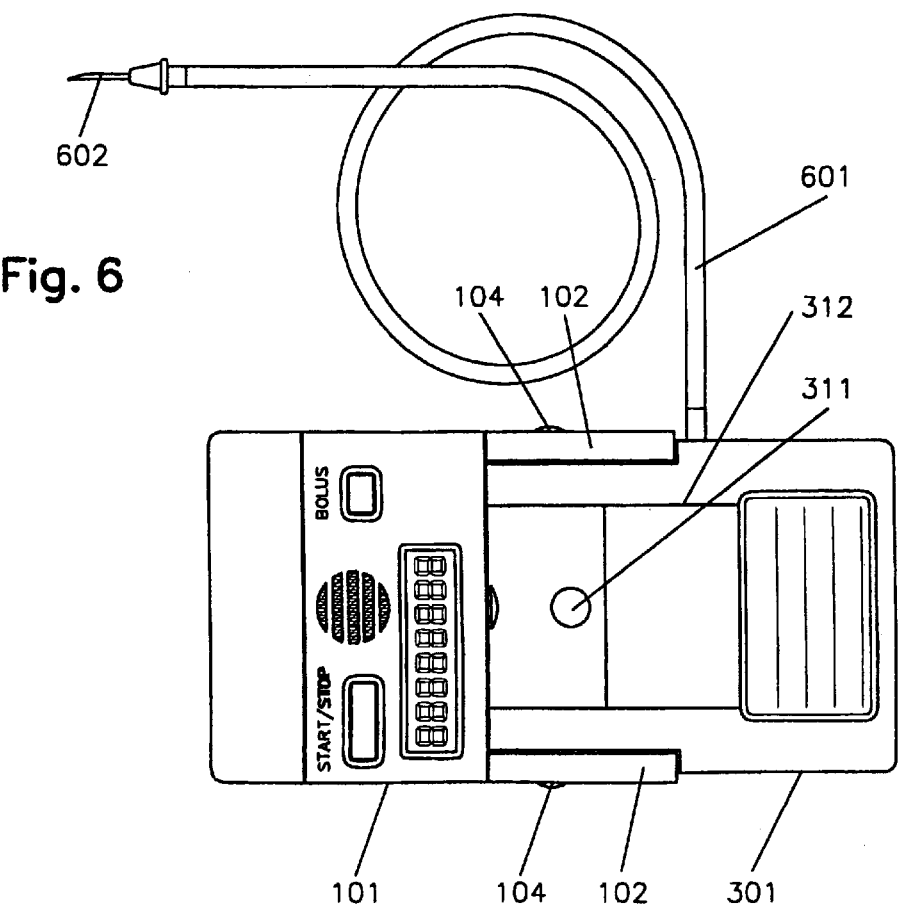
FIG. 6 is a general view of the assembled pump.
Figure 7:
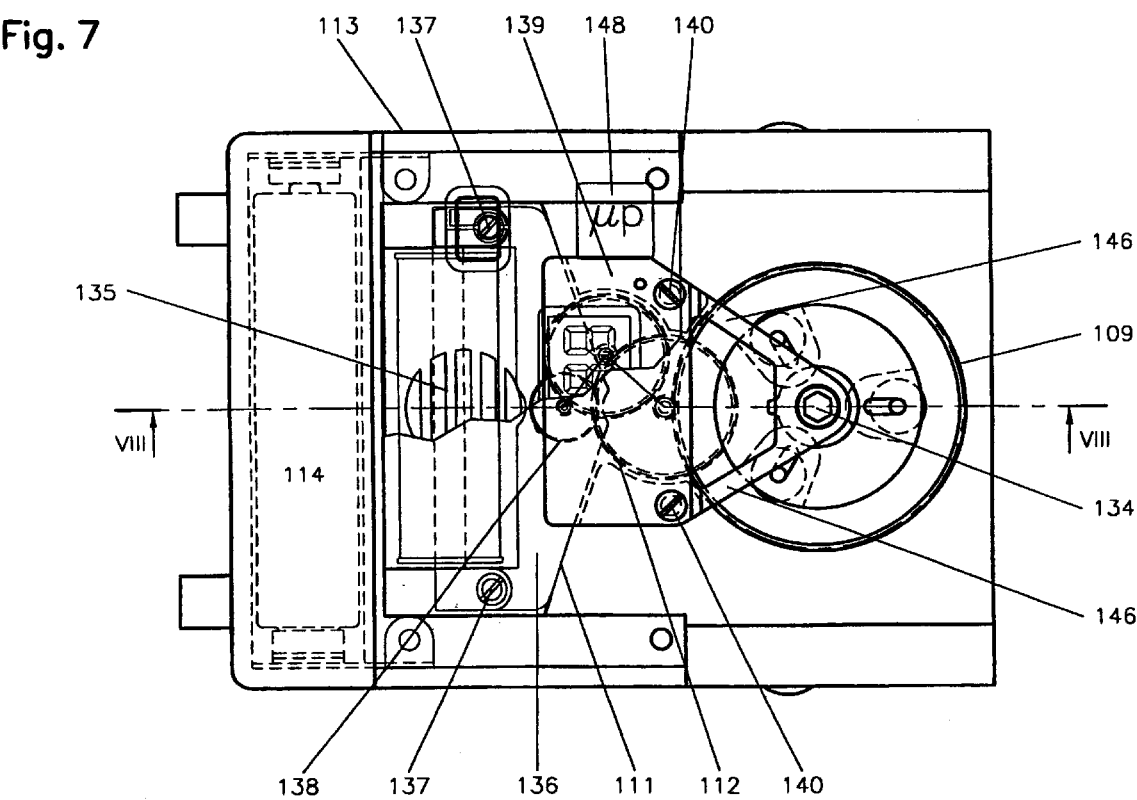
FIG. 7 is a top view of the pump unit.

We will now refer more specifically to FIGS. 4, 5, and 6, which show the manner in which the three units previously described connect to form the miniature pump according to the invention.

The reservoir unit 200 is placed first of all into the cassette unit 300. The plastic bag 201 is put into said first housing 301 while the flexible tubing 202 is positioned in channels 313 and 314, ensuring that its two rigid first and second connectors 204 and 205 are fitted into and clipped into first and second elbowed sections 315 and 316 respectively of plate 305. After having closed cover 302, all that remains is the insertion of the cassette into the sliders 102 of pump unit 100 until the third and fourth tongues 306 catch in the openings 103 (FIG. 5). The end of the lower part of rotor 109 occupies clearance 309 of plate 305 while the central section of flexible tubing 202 is automatically caught between rotor 109 and support piece 308. When the rotor is put into rotation in the direction of arrow F (counterclockwise), rollers 110 will alternately compress tubing 102 to push the solution that it contains to the outside.

The pump being loaded in this manner, stopper 203 of the tubing is removed and replaced as shown in FIG. 6 by tubing 601 which ends in a needle 602. Before inserting the latter into the patient, it is imperative to discharge the air still present in the circuit and to draw in the solution to be injected. As the normal rotation speed of rotor 109 is very slow (0.625 rpm), as will be described later on, this discharging operation must be done by rapidly turning the rotor by external means in order to not take too much time. The upper end of the shaft of the latter has, for this purpose, a shaped opening 134 appearing in opening 310 of the cassette and which permits, by means of an appropriate tool, the rapid rotation of the rotor until the droplets of solution to be injected come out of needle 602. The latter can then be inserted into the patient, after which the pump is started by pushing button 105 that controls the rotation of rotor 109 by mechanisms that will be described in detail below.

At the end of treatment, the uncoupling of pump unit 100 and cassette unit 300 takes place by pushing on the two buttons 104 so as to release the third and fourth tongues 306 of openings 103. The cassette can then be extracted by sliding it towards the outside before withdrawing thereof reservoir 200 which can be replaced by an other, the cassette and the pump being re-usable for another treatment.

Pump unit 100 will now be described referring to FIGS. 7 through 11 which show the rotor 109, a stepping motor 111, a gear train 112 connecting the motor to the rotor, an electronic control unit 113 and a small cylindrical battery 114.

Figure 8:
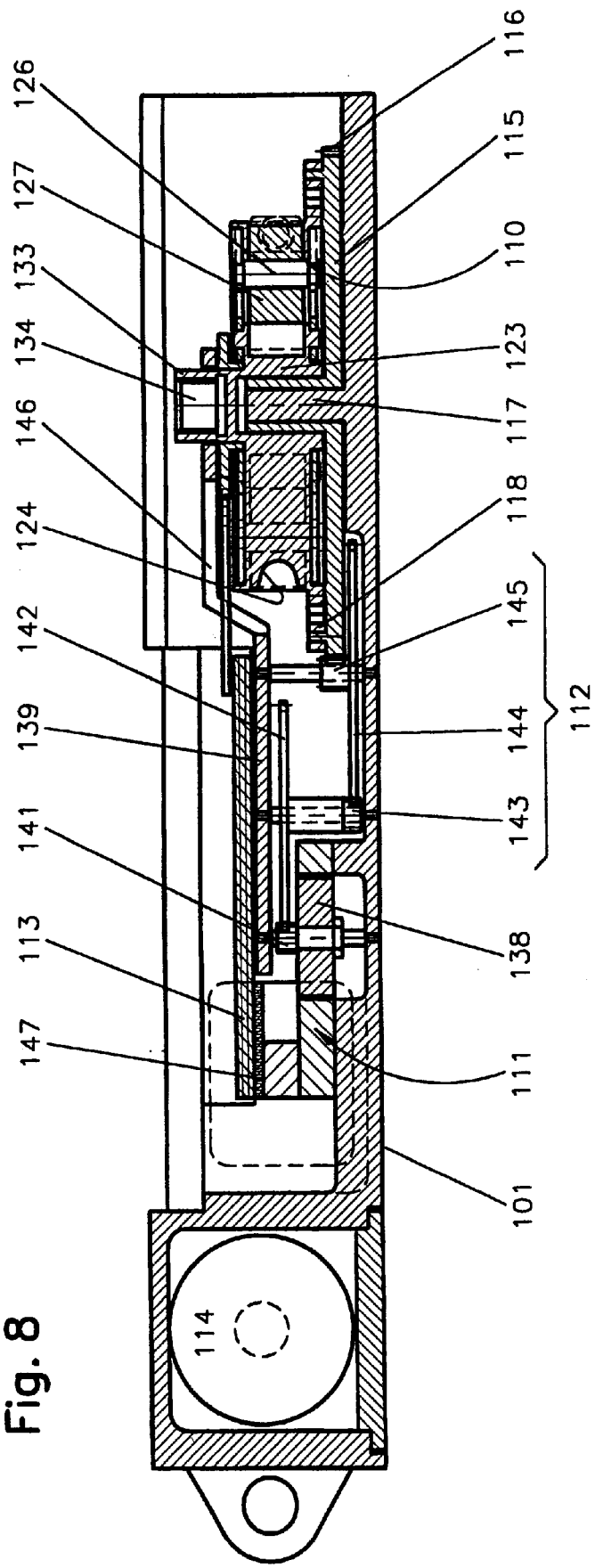
FIG. 8 is a cross section view of the pump unit according to line VIII—VIII of FIG. 7.
Figure 9:
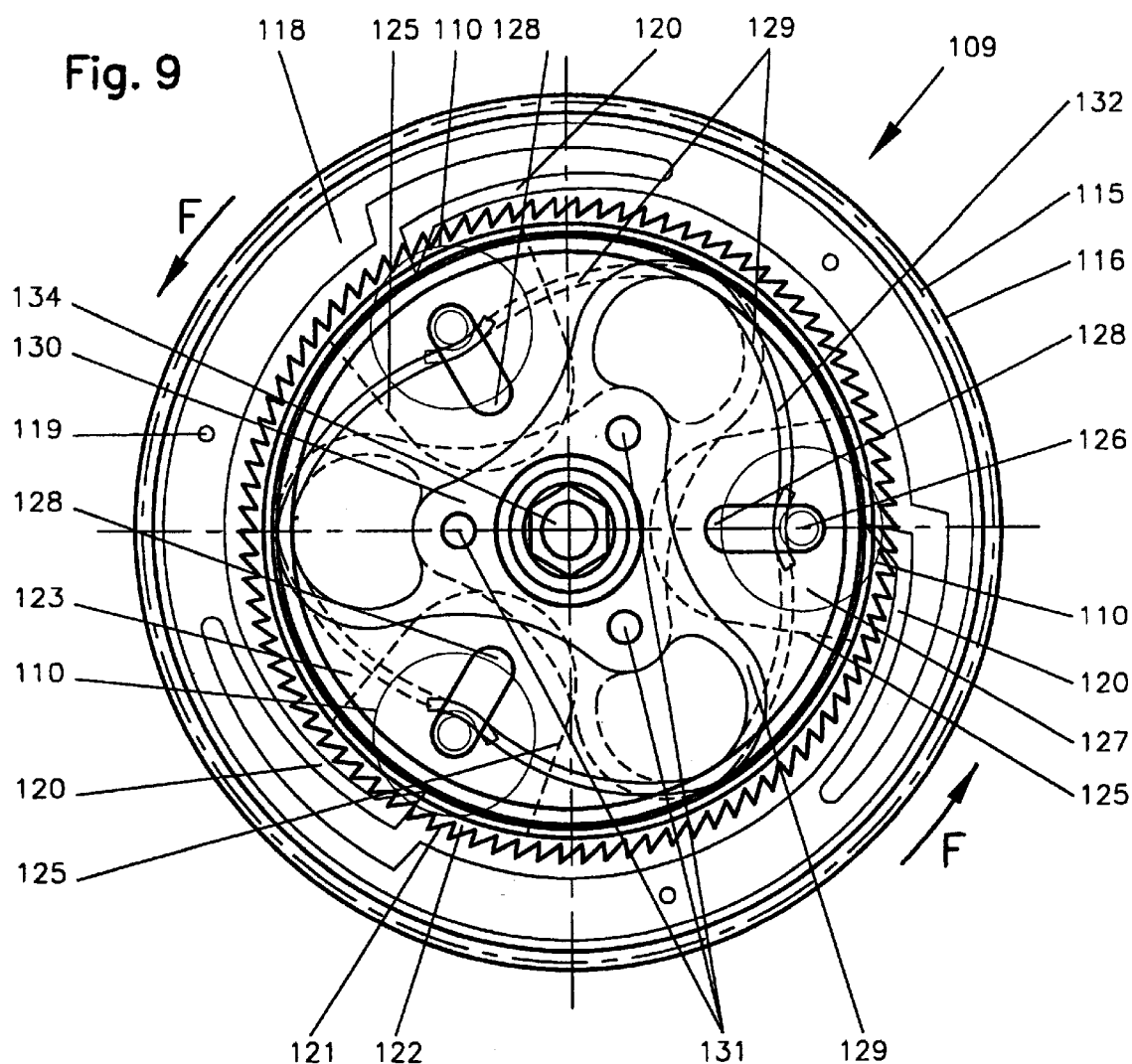
FIG. 9 is a top view of the rotor of the pump unit.

The rotor 109 shown in detail in FIGS. 8 and 9 includes a circular base 115 which has peripheral teeth 116 and is mounted freely rotating on a pivot 117 which is part of the bottom of case 101. A ring 118, of an external diameter which is slightly smaller than that of base 115, is mounted on the latter and affixed to it by pins 119. This ring has, towards the inside, three flexible arms 120 molded into its mass at 120 degrees one from the other and forming latches whose end interacts with the sawtooth periphery 121 of wheel 122. This latter constitutes the base of a cylindrical roller carrying plate 123 mounted on the axis of the base 115 around which it can turn freely.

The peripheral wall of plate 123 has a profile curved in towards the inside 124 in such a way as to form a channel for the flexible tubing 202. This same wall is also pierced by three housings 125 in the shape of a U, arranged at 120 degrees one from the other to accommodate the three pressure rollers 110 of the tubing.

Each roller 110 is formed by a shaft 126 and a cylindrical body 127 mounted on the shaft around which it can turn freely. The two ends of this shaft are fitted in oblong openings 128 arranged radially in the sections of the plate 123 which form the lower and upper flat walls of housing 125. The rollers are kept in a vertical position, i.e. with their axes parallel to the shaft of the rotor, and subjected to a radial force directed outward by means of two springs 129 arranged on each side of plate 123. Each spring includes a rigid central part 130, of a substantially triangular form, affixed to the plate concentrically to it by rivets 131 and three curved flexible spring arms 132 whose free ends rest on the respective ends of shafts 126 and push them outward in such a way that the rollers 110 exert a substantially constant force on tubing 202, which is set at 120 grams in the example described. The relative positioning errors of the rollers and the tubing, caused by inevitable manufacturing variations, are thus automatically compensated for, which avoids either excessive or insufficient compression of the tubing 202.

Plate 123 extends axially upward by a protrusion 133 traversing the central part 130 of the upper spring 129. This protrusion is pierced by the already mentioned shaped opening 134 into which fits, through the circular opening 310 of the cassette, the similarly shaped point of a tool (not shown) which permits the rapid rotation of the plate in order to discharge the pump.

Rotor 109 is put into rotation by the stepping motor 111 which is of the classic bipolar single-phase type and rotates at a speed of 16 rotations per second, at the rate of two steps per rotation. Its core coil and its stator, designated respectively by references 135 and 136, are affixed on feet formed in the base of case 101 by two screws 137. Its rotor 138 pivots between the base of the case and a bridge 139 affixed by screws 140 on feet that are part of the bottom of the case.

The rotor 138 carries a pinion 141 that meshes with a wheel 142 forming the first moving body of gear train 112. The pinion 143 of this wheel itself meshes with a wheel 144 whose pinion 145 finally meshes with the peripheral teeth 116 of the base 115 of rotor 109 in order to turn it at a speed of 0.625 rpm. Wheels 142 and 144 pivot, like rotor 138, between the bottom of the case and the link 139. The latter ends, after an elbow, in two arms 146, not shown in FIG. 9, whose common end includes a circular opening in which is held and in which pivots protrusion 133 of rotor 109.

During operation, when base 115 of the rotor is driven into the direction of arrow F by motor 111 through gear train 112, it turns with it ring 118 of which it is part. The three latches 120 of the latter then interact with the sawtooth periphery 121 of wheel 122 to put it into rotation, and along with it the roller-carrying plate 123 of which it forms the base. Thus, the rollers 110 compress tubing 102 one after the other to push the liquid that it contains into the direction of the injection needle 602.

When, to discharge the tubing, one causes the roller-carrying plate 123 to turn by means of an appropriately shaped tool introduced into opening 134, the base 115 and ring 118 become fixed, because they are restrained by the retention torque of motor 111 and its gear train 112. Disengagement then occurs automatically between ring 118 and wheel 122 due to the fact that the rotation of the latter causes the expulsion of the three latches 120 of sawtooth teeth 121. The roller-carrying plate 123 can thus be turned rapidly without any effect on the gear train or the motor.

Figure 10:
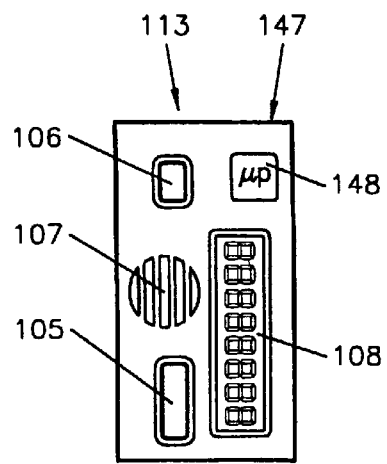
FIG. 10 shows the electronic control unit of the pump.

The electronic control unit 113, shown in FIG. 10, has as its base a printed circuit board 147, affixed under the upper face of the case and possessing buttons 105 and 106, the sound warning 107 and the LCD display 108. The board also has a microprocessor circuit 148 integrating the following main functions: voltage doubler, quartz time base, memory, LCD driver and sound generator. This microprocessor being of a known type, such as EPSON 62L35, will not be described in detail.

Figure 11:
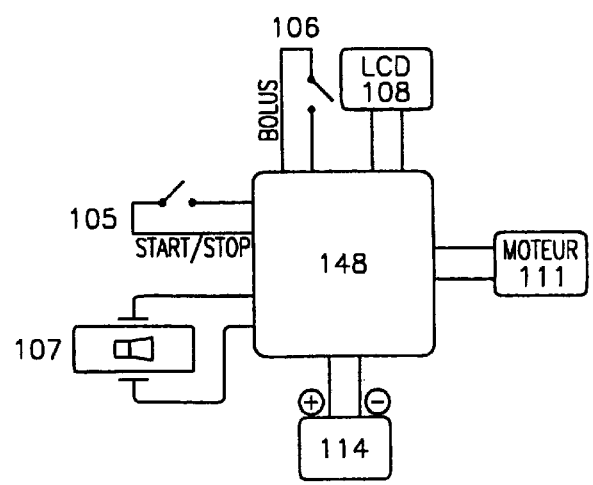
FIG. 11 is a diagram of the control circuit of the pump.

The whole of these components as well as battery 114 and the coil of motor 111 are interconnected according to the simplified diagram of FIG. 11.

The microprocessor 148 is programmed according to methods well known by the expert to make the whole unit function as follows.

When switch 105 is activated for the first time, it triggers the operation of microprocessor 148 which, under the direction of a control program recorded in memory, applies drive impulses at a frequency of 32 Hz to the terminal of the stepping motor 111, triggering its rotation at a speed of 16 rpm. The roller-carrying rotor 109 is then driven at a speed of 0.625 rpm. The operation of the pump is interrupted when switch 105 is activated a second time.

For example, with a rotation radius of the roller-carrying plate of 10.44 mm and a speed of 0.625 rpm, the solution flows through the tubing at a speed of 41 mm/min. By choosing tubing with a 1.47 mm internal diameter, the instantaneous output of the pump is thus 69.54 mm$^3$/minute, or 100 cm$^3$ per day.

The microprocessor 148 also permits, in response to pushing button 106, the bypassing of the control program put into memory, to permit the injection of a specific additional quantity of solution (bolus). This procedure is specifically intended for pain-relief treatment.

The pump is also equipped with mechanisms permitting the activation of the audible warning 107 and/or LCD display 108 in case of malfunction: failure to respect the program, stoppage, obstruction of needle, depletion of battery . . . . Since these mechanisms are not the subject of this patent, they will not be described.

We will finally refer to FIG. 12, which shows a design variation of cassette unit 300 for treatments requiring injection of large amounts of solution. The cassette can certainly be extended to accommodate a larger reservoir, but if the volume of the latter exceeds 20 ml, the overall dimensions of the pump risk making it impractical. For this reason, the cassette unit of FIG. 12 contains only plate 305 described in FIG. 3, the same references being used to designate the same elements. The reservoir unit then includes a large volume bag 206 which is not fitted into the cassette but merely connected to it by longer flexible tubing 202 identical to that described in FIG. 2.

What is claimed is:

1. A miniature peristaltic pump comprising:
    a rotor (109) equipped with three rotating rollers (110) each roller comprising a substantially cylindrical body (127) and a shaft (126) on which said body is rotatably mounted, wherein the ends of the shafts of the rollers fit into oblong openings (128) arranged radially in the rotor,
    a means for driving (111, 112) said rotor,
    a means for controlling (113) said driving means,
    a support piece equipped with a rounded-off portion (308) arranged in a substantially concentric manner to the rotor and against which, during operation, said rollers compress a flexible tubing (202) connected to a solution reservoir (201) pushing the solution towards the outside and
    a means for automatically compensating, by means of springs, the gaps in position between the rollers and said support piece,
    wherein said means for automatically compensating comprises two springs (129) arranged at the level of the respective ends of said shafts and comprise a central part (130) concentric to the rotor and three curved spring arms (132), one for each roller, of which one end is connected to said central part and the other end is supported on the corresponding end of a roller shaft for pushing it towards the outside and towards the tubing, whereby each roller exerts a substantially constant compression force on the tubing.

2. A miniature peristaltic pump according to claim 1, wherein the rotor and its rollers, said driving means and said controlling means form a pump unit (100), wherein the support piece is part of a cassette unit (300), wherein said pump and cassette units are each equipped with means permitting their connection and the cassette unit comprises a means for holding the tubing (202) interchangeably, wherein the tubing is an indissociable part of the reservoir (201) and wherein the means for holding automatically positions said tubing so that it fits against said rounded-off section (308) at the moment of connection of the pump and cassette units to be compressed by said rollers; the tubing and reservoir thus forming a reservoir unit (200) which is exchangeable for another reservoir unit after use.

3. A miniature peristaltic pump according to claim 2, wherein the cassette unit (300) comprises a plate (305) which fits like a drawer into the pump unit and is pierced by a generally U-shaped housing (307), shaped and sized to surround the rotor and whose rounded-off base (308) forms the support piece of the tubing, and wherein the means for holding said tubing comprises a first (313) and a second channel (314) arranged along the respective sides of said plate, said channels having an end opened on the outside of the plate and their other ends emerging opposite one from the other in the inside of said housing.

4. A miniature peristaltic pump according to claim 3, wherein said channels comprise means for retaining said tubing by clipping.

5. A miniature peristaltic pump according to claim 4, wherein said means for retaining the tubing comprise elbowed parts (315, 316) of said channels, shaped and sized so that connectors (204, 205) of corresponding shape of said tubing are fitted and retained there by clipping.

6. A miniature peristaltic pump according to claim 2, wherein the cassette unit is fixed into the pump unit by clipping its plate into sliders (102) of said pump unit.

7. A miniature peristaltic pump according to claim 2, wherein the cassette unit further comprises a housing (301) to accommodate the solution reservoir.

8. A miniature peristaltic pump according to claim 1, further comprising a means for turning said rotor through an external action for discharging from the tubing.

9. A miniature peristaltic pump according to claim 8, wherein the rotor comprises two superimposed concentric parts, wherein the first part is connected to said means for driving and the second part carries the rollers, and wherein said pump further comprises an engaging-disengaging means, wherein, during normal operation, its two parts engage for producing its rotation through its driving means, and when it is put into rotation by an external action, the said parts are automatically disengaged.

10. A miniature peristaltic pump according to claim 9, wherein the first part of the rotor comprises a first toothed wheel (115), cooperating with said means for driving, while the second part comprises a second toothed wheel (122) forming the base of a roller-carrying plate (123) and wherein said engaging-disengaging means comprise a ring (118) concentrically affixed to the first toothed wheel (115) of the first part, and surrounding the second toothed wheel (122) of the second part, and wherein the engaging-disengaging means comprises towards the interior three flexible arm (120) forming latches, the ends of which cooperate with the second toothed wheel of the second part.

11. A miniature peristaltic pump according to claim 8, wherein the means for turning the rotor through an external action comprises a protrusion (133) which extends from the shaft of the rotor and is pierced by an shaped opening (134) for accommodating the end of a tool of corresponding shape.

12. A miniature peristaltic pump comprising:

a rotor (109) equipped with three rotating rollers (110) each roller comprising a substantially cylindrical body (127) and a shaft (126) on which said body is rotatably mounted, wherein the ends of the shafts of the rollers fit into oblong openings (128) arranged radially in the rotor, a driver (111, 112) of said rotor, a controller (113) of said driver, a support piece equipped with a rounded-off portion (308) arranged in a substantially concentric manner to the rotor and against which, during operation, said rollers compress a flexible tubing (202) connected to a solution reservoir (201) for pushing the solution towards the outside and a spring compensator which automatically adjusts the gaps in position between the rollers and said support piece, wherein said spring compensator comprises two springs (129) arranged at the level of the respective ends of said shafts and comprise a central part (130) concentric to the rotor and three curved spring arms (132), one for each roller, of which one end is connected to said central part and the other end is supported on the corresponding end of a roller shaft for pushing it towards the outside and towards the tubing, whereby each roller exerts a substantially constant compression force on the tubing.

13. A miniature peristaltic pump according to claim 12, wherein the rotor and its rollers, said driver and said controller form a pump unit (100), wherein the support piece is part of a cassette unit (300), wherein said pump and cassette units are each equipped with connecting devices of the units and the cassette unit comprises a holder of the tubing (202), wherein the tubing is an indissociable part of the reservoir (201) and wherein the holder automatically positions said tubing for fitting against said rounded-off section (308) when the pump and cassette units are connected to be compressed by said rollers; the tubing and reservoir thus forming a reservoir unit (200) which is exchangeable for another reservoir unit after use.

14. A miniature peristaltic pump according to claim 13, wherein the cassette unit (300) comprises a plate (305) which fits like a drawer into the pump unit and is pierced by a generally U-shaped housing (307), shaped and sized for surrounding the rotor and whose rounded-off base (308) forms the support piece of the tubing, and wherein the holder of said tubing comprises a first (313) and a second channel (314) arranged along the respective sides of said plate, said channels having an end opened on the outside of the plate and their other ends emerging opposite one from the other in the inside of said housing.

15. A miniature peristaltic pump according to claim 14, wherein said channels comprise retainers which retain said tubing by clipping.

16. A miniature peristaltic pump according to claim 15, wherein said retainer of the tubing comprises elbowed parts (315, 316) in said channels, shaped and sized so that connectors (204, 205) of corresponding shape of said tubing are fitted and retained in the retainer by clipping.

17. A miniature peristaltic pump according to claim 13, wherein the cassette unit is fixed into the pump unit by clipping its plate into sliders (102) of said pump unit.

18. A miniature peristaltic pump according to claim 13, wherein the cassette unit further comprises a housing (301) of the solution reservoir.

19. A miniature peristaltic pump according to claim 12, further comprising a turner of said rotor through an external action which discharges solution from the tubing.

20. A miniature peristaltic pump according to claim 19, wherein the rotor comprises two superimposed concentric parts, wherein the first part is connected to said driver and the second part carries the rollers, and wherein said pump further comprises a clutch, wherein the clutch engages the first and second parts for rotating the second part by the driver and disengages the first and second parts when said turner is used for discharging solution from the tubing.

21. A miniature peristaltic pump according to claim 20, wherein the first part of the rotor comprises a first toothed wheel (115) which is driven by said driver and the second part comprises a second toothed wheel (122) which forms the base of a roller-carrying plate (123), and wherein said clutch comprises a ring (118) concentrically affixed to the first toothed wheel (115) of the first part and surrounding the second toothed wheel (122) of the second part, and wherein the clutch comprises towards the interior three flexible arms (120) which form latches, the ends of which engage the second toothed wheel of the second part.

22. A miniature peristaltic pump according to claim 19, wherein the turner of the rotor through an external action comprises a protrusion (133) which extends from the shaft of the rotor and is pierced by an shaped opening (134) for engaging a tool.

* * * * *